US012714309B2

(12) United States Patent
Zhang et al.

(10) Patent No.: US 12,714,309 B2
(45) Date of Patent: Aug. 25, 2026

(54) MAGNETIC TOLERANT IMAGING

(71) Applicant: Worcester Polytechnic Institute, Worcester, MA (US)

(72) Inventors: Haichong Zhang, Shrewsbury, MA (US); Ryo Murakami, Worcester, MA (US); Gregory S. Fischer, Needham, MA (US); Yang Wang, Shrewsbury, MA (US); Ryosuke Tsumura, Saitama (JP)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 18/962,176

(22) Filed: Nov. 27, 2024

(65) Prior Publication Data

US 2025/0169697 A1 May 29, 2025

Related U.S. Application Data

(60) Provisional application No. 63/602,755, filed on Nov. 27, 2023.

(51) Int. Cl.

| | |
|---|---|
| ***A61B 5/00*** | (2006.01) |
| ***A61B 5/055*** | (2006.01) |
| *A61B 90/00* | (2016.01) |

(52) U.S. Cl.

CPC .......... *A61B 5/0035* (2013.01); *A61B 5/0095* (2013.01); *A61B 5/055* (2013.01); *A61B 5/6852* (2013.01); *A61B 2090/364* (2016.02); *A61B 2576/00* (2013.01)

(58) Field of Classification Search

CPC ..... A61B 5/0035; A61B 5/0095; A61B 5/055; A61B 5/6852

See application file for complete search history.

(56) References Cited

U.S. PATENT DOCUMENTS

2007/0015969 A1* 1/2007 Feldman .............. A61B 5/0084 600/160

2016/0022146 A1* 1/2016 Piron .................. A61B 5/0059 600/411

* cited by examiner

*Primary Examiner* — Joel F Brutus

(74) *Attorney, Agent, or Firm* — Armis IP Law, LLC

(57) ABSTRACT

A magnetic tolerant, multi-mode imaging device includes an elongated probe adapted for insertion into an imaging region of a first imaging modality, and an imaging sensor in rotational communication with the elongated probe, where the imaging sensor is responsive to a second imaging modality. A control circuit is configured for activating the first imaging modality and the second imaging modality for imaging over a region of interest, and an imaging circuit aligns images received from the first and second imaging modalities for registration in a common frame of reference to render a combined image.

13 Claims, 6 Drawing Sheets

140
122
Linear Array (rotate with inner shaft)
Bearing
125
Bearing
125
Rotation Axis
(both Outer & Inner Shafts)
127
110
111
126
130
Mirror Stage
(rotate with Outer Shaft)
Dielectric Mirror
(rotate with outer shaft)
Top View 140
122
Laser
114
Acoustic Wave
128
Bearing
125
Bearing
125
Rotation Axis
(both Outer & Inner Shafts)
127
110
111
115
134
130
Side View

MAGNETIC TOLERANT IMAGING

RELATED APPLICATIONS

This patent application claims the benefit under 35 U.S.C. § 119(e) of U.S. Provisional Patent App. No. 63/602,755, filed Nov. 27, 2023, entitled "MAGNETIC TOLERANT IMAGING," incorporated herein by reference in entirety.

STATEMENT OF FEDERALLY SPONSORED RESEARCH AND DEVELOPMENT

This invention was made, at least in part, with U.S. Government support under Contract Nos. NIH DP-5 OD028162 and R01 EB030539, both awarded by the National Institute for Health (NIH). The Government has certain rights in the invention.

BACKGROUND

Modern medical technology embraces various types of imaging for noninvasively visualizing internal anatomical structures. Certain medical contexts suggest an assessment of the structural, functional, metabolic and molecular information of a target is to achieve image-guided diagnosis/intervention with higher sensitivity and specification, but each of Magnetic Resonance Imaging (MRI), Photoacoustic (PA), and Ultrasound (US) may not individually cover all the requirements needed or expected for a particular imaging task. A framerate of MRI is limited and usually not able to provide video-like real-time imaging rates, however photoacoustic and ultrasound provide higher framerate and a real-time monitoring capability. Since MRI involves strong magnetic fields, the MRI sensing environment should be kept free of ferrous metals.

SUMMARY

A multi-mode imaging system includes an elongated probe adapted for insertion into a magnetic resonance imaging (MRI) region, where the elongated probe has a body having a tapered or rounded distal end adapted for insertion into an imaging subject defining the region of interest, and an inner shaft disposed within a bore of the body. A photoacoustic imaging array attached to the inner shaft inserted concentrically into the probe and in rotational communication with the elongated probe allows independent rotation. The photoacoustic imaging array is responsive to photoacoustic signals for generating an imaging plane through a reflective mirror attached at a distal end of the body adjacent the photoacoustic imaging array. The inner shaft is configured for rotation independently of the reflective mirror for varying the imaging plane about an axis, as the photoacoustic imaging array rotates independently of the mirror for gathering a set of images in a plane perpendicular around the rotation axis. A photoacoustic laser disposed on the inner shaft emanates a laser signal directed at the reflective mirror for generating a PA response; alternatively a pure ultrasound signal may be emanated, reflected and gathered. An imaging circuit aligns images received from the PA imaging plane with an imaging signal based on the magnetic resonance imaging for rendering a combined image.

Configurations herein are based, in part, on the observation that medical imaging is a widely used technology that performs non-invasive visualization of internal anatomy and structures for medical diagnoses and treatment. Many modalities of imaging are available, and their selection typically depends on a usage context, imaged details sought by the imaging, and patient constraints, i.e. X-ray imaging cannot be used during pregnancy. Unfortunately, conventional approaches to medical imaging suffer from the shortcoming that different imaging modalities exhibit varied feature details and discrimination of features, and selection of a particular imaging modality, such as MRI, photoacoustic, ultrasound, X-ray and the like may not render all features and detail needed for a particular task.

Accordingly, configurations herein substantially overcome the shortcomings of conventional imaging by combining multiple imaging modalities over an imaging region of interest, and co-registering the gathered imaging signals with a common frame of reference to render an image with features from each of the imaging modalities invoked. In a particular configuration, a non-metallic photoacoustic probe operates in an MRI imaging field, and gathers photoacoustic and ultrasound images of the imaging region while disposed in an MRI imaging field. The resulting images of the imaging region are aligned by registration with a common frame of reference to render features of all modalities.

In further detail, a magnetic tolerant, multi-mode imaging device includes an elongated probe adapted for insertion into an imaging region of a first imaging modality, and an imaging sensor in rotational communication with the elongated probe, where the imaging sensor responsive to a second imaging modality. A control circuit is configured for activating the first imaging modality and the second imaging modality for imaging over a region of interest, and an imaging circuit for aligning images received from the first and second imaging modalities for registration in a common frame of reference to render a combined image.

BRIEF DESCRIPTION OF THE DRAWINGS

The foregoing and other features will be apparent from the following description of particular embodiments disclosed herein, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
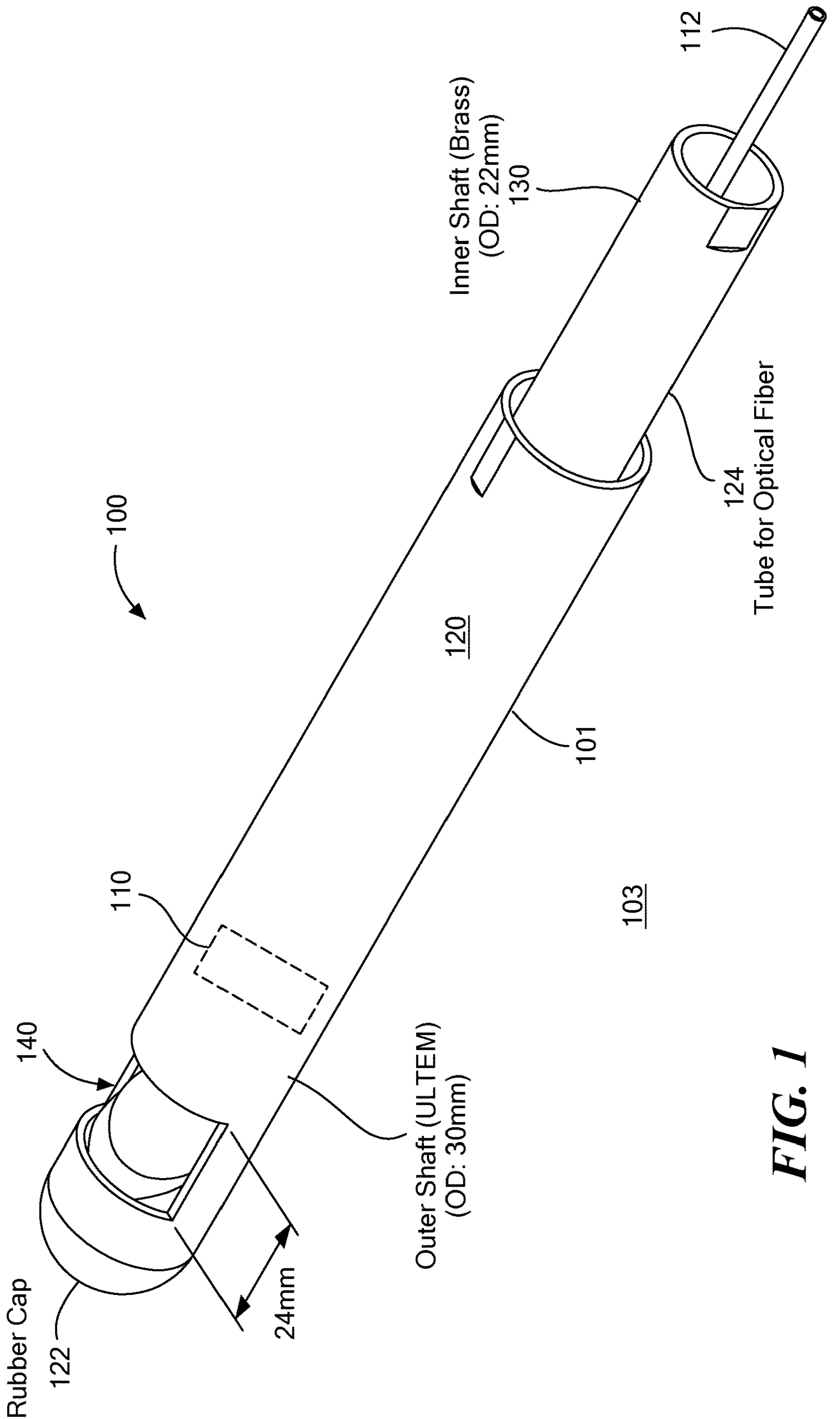
FIG. 1 is a perspective view of a magnetic tolerant, multi-mode imaging device as defined herein.

Configurations herein depict an example MRI-compatible photoacoustic/ultrasound (PA/US) imaging platform to improve the diagnosis of certain ailments such as prostate cancer (PC). In the proposed solution, PA imaging, which offers real-time, non-ionizing imaging with high sensitivity and specificity, is combined with MRI, aiming to overcome PA's limited field of view (FOV) and make PA scalable for translation to clinical settings. Central to the design of the system is a reflector-based transrectal probing mechanism composed of MRI-compatible materials. A linear transducer with a center hole for optical fiber delivery can be mechanically actuated to form a multi-angled scan, allowing PA/US imaging from varied cross-sectional views.

In a particular target application for the multi-modal probe, PCa is known as one of the most prevalent and fatal cancer types. An MRI-compatible photoacoustic/ultrasound (PA/US) imaging platform described herein improves the diagnosis of PCa. In the proposed solution, PA imaging, which offers real-time, non-ionizing imaging with high sensitivity and specificity, is combined with MRI, aiming to overcome PA's limited field of view (FOV) and make PA scalable for translation to clinical settings. Central to the design of the system is a reflector-based transrectal probing mechanism composed of MRI-compatible materials. The linear transducer with a center hole for optical fiber delivery can be mechanically actuated to form a multi-angled scan, allowing PA/US imaging from varied cross-sectional views. MRI compatibility of the system can be assured and feasibility of tri-modal imaging capability shown by visualizing a tubing phantom containing contrast agents. The ex-vivo evaluation of targeted tumor imaging capability was performed with a mouse liver sample expressing PSMA (prostate-specific membrane antigen-positive) tumors, affirming the system's compatibility in spectroscopic PA (sPA) imaging with biological tissue. These results support the feasibility of the in-bore MRI-compatible transrectal PA and US and the potential clinical adaptability.

In this manner, MRI, PA, and US imaging can be performed concurrently without any relocation of a patient. This avoids movement/deformation of targeted anatomy, resulting in a direct combination of the three imaging modalities. The MRI, PA, and US images can be co-registered. The live images or information obtained from the imaging (e.g. tumor or ablation boundaries) or one modality may be overlaid on live imaging from the other modalities. The combined PA/US probe or associated structure may contain imaging fiducials to enable localization of the PA/US device (and its associated images) with respect to the MRI imaging system's acquired images. The system may be configured such that the transrectal combined PA/US probe or associated structure also incorporates MRI imaging coils (e.g. one or more MR receive coils) so as to improve MR image quality in the same vicinity as the PA and US imaging.

FIG. 1 is a perspective view of a magnetic tolerant, multi-mode imaging device as defined herein. Referring to FIG. 1, a magnetic tolerant, multi-mode imaging device and system 100 includes an elongated probe 101 adapted for insertion into an imaging region of a first imaging modality, and an imaging sensor 110 in rotational communication with the elongated probe 101, such that the imaging sensor 110 is responsive to a second imaging modality.

In an example configuration, where the probe 101 is configured for transrectal examination in a PCa patient, the elongated probe 101 further comprises a body 120 having a tapered or rounded distal end 122 adapted for insertion into an imaging subject defining the region of interest. An inner shaft 130 is disposed within a bore 124 of the body 120, and the imaging sensor 110 is disposed on the inner shaft 130 for rotation, shown further below. In the example configuration, the first imaging modality is magnetic resonance imaging and the elongated probe 101 is disposed in an imaging region of a magnetic resonance region 103, such as deployed in a patient engaged in an imaging bore of an MRI enclosure.

A control circuit is configured for activating the first imaging modality and the second imaging modality, such as via the PA laser optical fiber 112 for imaging over a target region of interest, and an imaging circuit aligns images received from the first and second imaging modalities for rendering a combined image. When MRI is one of the imaging modalities, the probe 101, including the body 120 and the inner shaft 130, are formed from magnetic tolerant materials; indeed, for effective MRI deployment, the entire elongated probe 101 is formed from non-magnetic materials.

Transrectal PA imaging apparatus have been attempted, however, the cross-validation, with other complementary imaging modalities is not straightforward because of the tissue deformation and alignment difficulty with data taken in different settings, especially with MRI due to the requirement of the device MRI compatibility, i.e. non ferrous metals. Second, PA imaging has an inconsistent, restricted field of view (FOV) compared to MRI or PET (positron emission tomography), because the ultrasound receiver geometry determines the imaging field. This makes registering US/PA imaging with other preoperative imaging devices challenging. Deployment of the PA-guided procedure to be scalable and compatible with other imaging modalities, especially MRI, alleviates these constraints.

In the PCa example introduced above, while MRI and PET/CT are known for their high sensitivity and specificity in PCa imaging, they may not be capable of providing a sufficient frame rate for real-time intraoperative biopsy guidance and often are conducted independently. Given the inherent limitations of conventional imaging techniques, there is a need for developing an imaging modality that offers non-ionizing, real-time PCa imaging with high sensitivity and specificity. Photoacoustic (PA) imaging is an emerging non-ionizing imaging technique that integrates the benefits of optical and US imaging. Spectroscopic PA (sPA) provides quantification of multiple indices, which can contribute valuable insights into cancer severity and prognosis. Prostate-specific membrane antigen (PSMA) is a receptor on the surface of PCa cells. It is characterized by its strong correlation with aggressive tumors. In addition to its functional imaging abilities, PA imaging, inclusive of sPA, has been demonstrated to be effective for real-time monitoring. These attributes position PA imaging as a promising modality for PCa diagnosis.

Figure 2A:
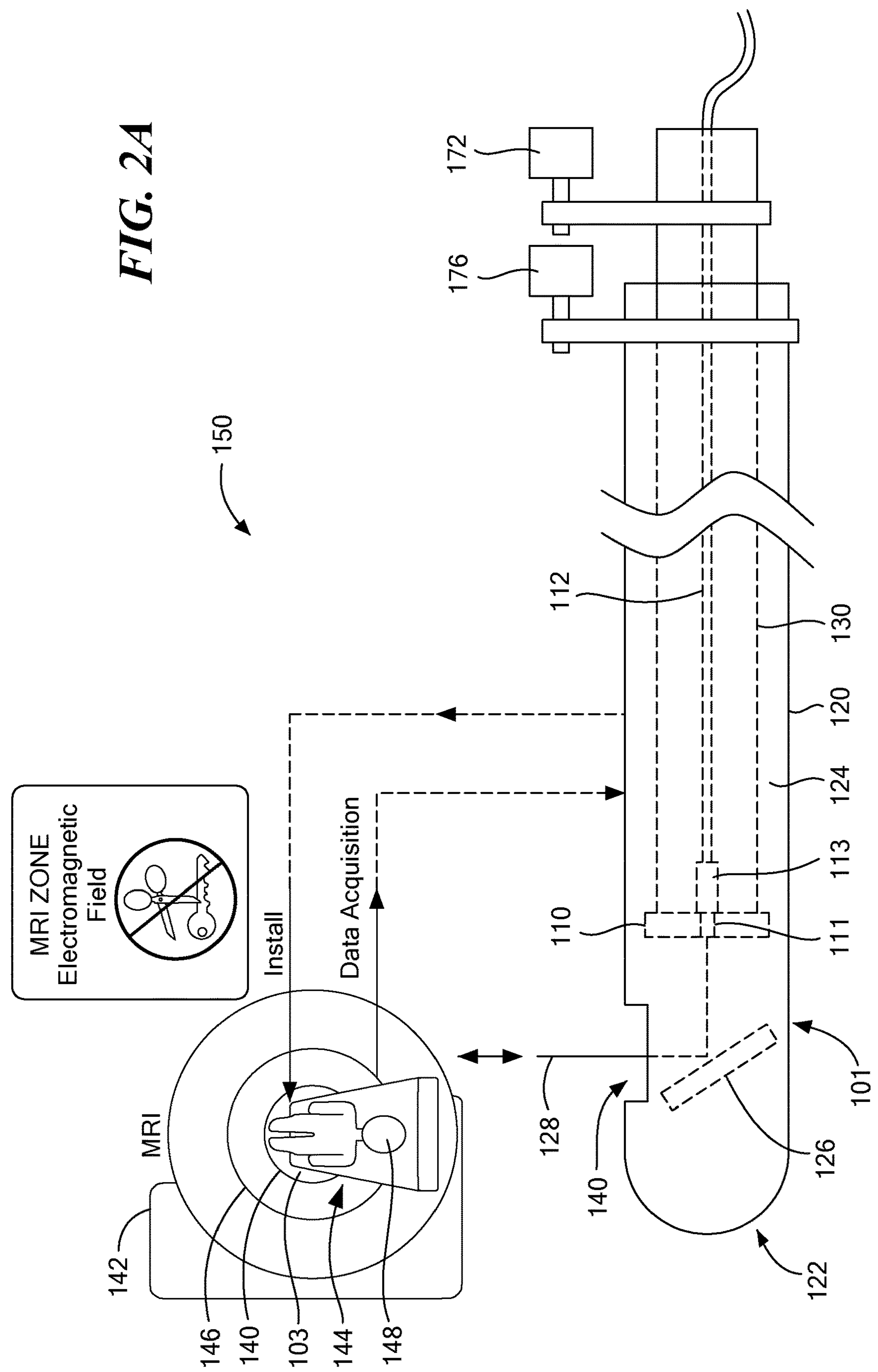
FIGS. 2A-2C are a schematic view of the multi-mode imaging device as in FIG. 1.
Figures 2B, 2C:
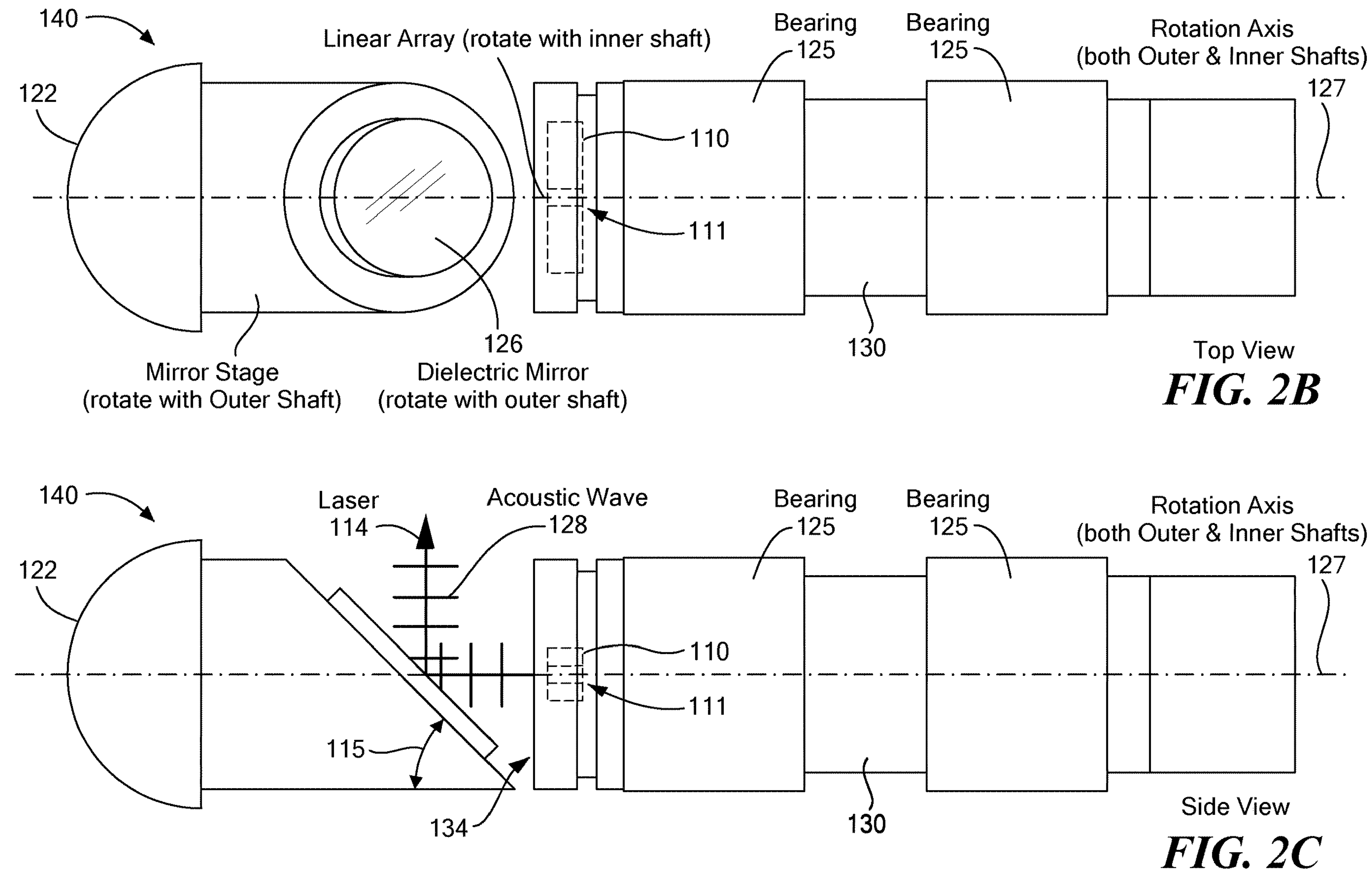

FIGS. 2A-2C are a schematic view of the multi-mode imaging device as in FIG. 1. Referring to FIGS. 1-2C, the MRI-compatible PA/US imaging platform is shown. The representative system is illustrated in FIG. 2A. In this approach, the PA/US imaging probe 101 is placed inside the MRI bore 140 so that these three imaging modalities can be performed without relocating patients. The MRI 142 modality yields broad FOV images, effectively serving as a global reference for the local imaging supplied by the PA/US imaging. Despite the non-real-time nature of MRI scanning, this approach enables on-demand updates of MRI images, a feature previously unattainable when the PA/US apparatus lacked MRI compatibility, requiring patient movement between the MRI suite and the PA/US room. Leveraging the supplementary role of MRI 142, it is anticipated that the approach is adaptable to larger subjects, facilitating the further exploration of the clinical translatability of PA imaging.

In FIG. 2A, a side transparent view of the probe 101 is shown, having a reflective mirror 126 disposed within the body 120 distal from a terminus of the inner shaft 130, such that the reflective mirror 126 is configured for reflecting the image signal 128 of the second imaging modality. The inner shaft 130 is therefore adapted for rotation independently of the reflective mirror 126 and body 120/outer shaft. One or more bearings 125 smooth concentric rotation of the inner shaft 130 within the body 120 around a rotation axis 127.

In FIGS. 2A-2C, the reflective mirror 126 is shown attached to the body 120 adjacent the distal end 131 of the inner shaft and oriented at an angle, typically around 45°. A photoacoustic laser is disposed on the inner shaft 130 for emanating a laser signal 114 emanating from optic fiber 112. The reflective mirror 126 is disposed for directing the laser signal based on the angle 115 of the reflective mirror 126. The dielectric mirror 126 is fixed to the outer shaft and the mirror typically has a 45-degree slope with respect to the horizontal axis of rotation 127. The mirror is designed so that it can reflect both the acoustic wave and the laser, altering their trajectories by 90°.

The mirror 126 therefore reflects both the laser signal 114 and acoustic wave 128 perpendicular to the probe 101 and rotation axis 127. As the inner shaft 130 and body 120 independently rotate to define the probe 101, direction of the perpendicular signals likewise rotate, discussed further below in FIGS. 4A and 4B. A void 140 in the body 120 allows reflection of the laser signal 114 into the region of interest. The inner shaft 130 disposes the photoacoustic sensor 110, such that the photoacoustic sensor 110 is aligned with the reflective mirror 126 and the photoacoustic laser for receiving reflected photoacoustic signals 128 from the region of interest. The laser is complemented by an aperture 111 for allowing the laser signal 114 to pass through the photoacoustic sensor 110 or array.

Figure 3A:
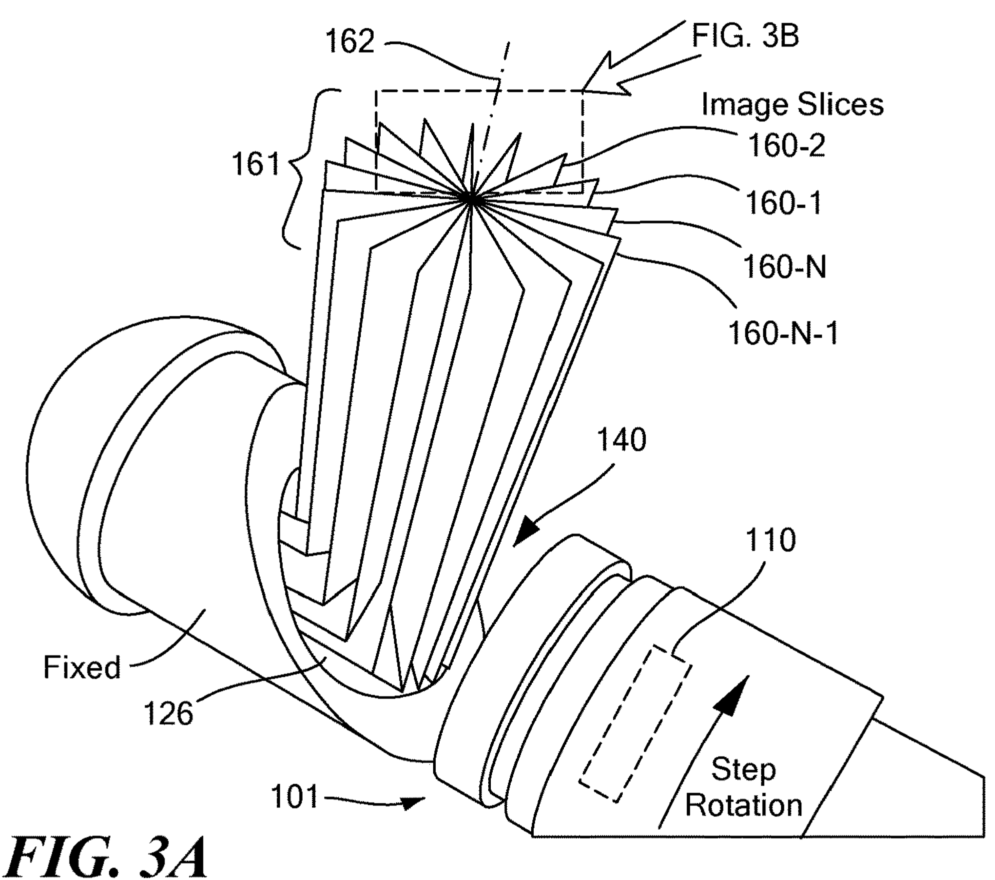
FIGS. 3A and 3B shows an orientation of image planes gathered by the multi-mode imaging device of FIGS. 1 and 2A-2C.
Figure 3B:
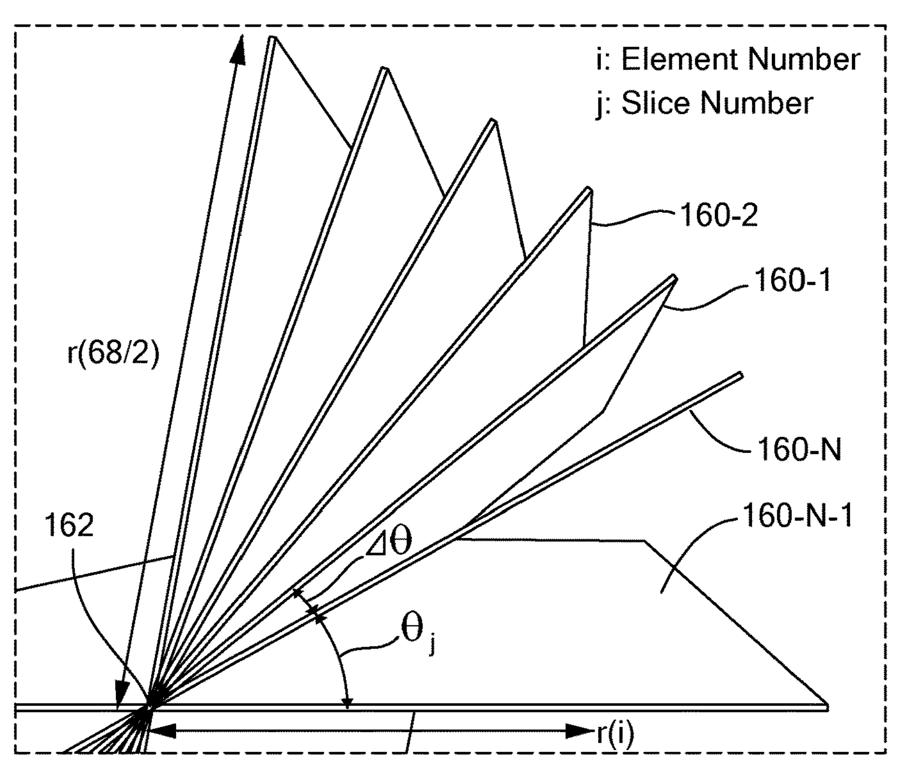

FIGS. 3A and 3B show an orientation of image planes gathered by the multi-mode imaging device of FIGS. 1 and 2. Referring to FIGS. 1-3B, the imaging probe 101 is designed so that the rotation of the linear transducer (sensor 110) enables the multi-angled scan of 2D PA/US images, shown in FIG. 3A. The acquired imaging slices 161 are allocated to their corresponding angles, shown in the top view of the image slices in FIG. 3B. Here, i is the transducer element number from the center of rotation and j is the slice number. In the example configuration, since the linear array has 68 elements in total, the maximum number of i is 34. As the number of imaging slices for this scanning increases, the distance between the slices becomes smaller, determining the scanning density in the 3D space. During the rotation, the mirror 126 attached to the outer probe shaft is fixed. In PA, 64 frames are obtained for each slice and wavelength, and the total number of wavelengths applied is six (730, 750, 780, 800, 820, and 850 nm).

The imaging sensor 110 may be a photoacoustic array 110', such that the photoacoustic array 110' is configured for returning an imaging signal indicative of an imaging plane designated as a slice 160-1 . . . 160-N (160 generally). A sensor drive circuit rotates the inner shaft 130 about the axis 127 for gathering the set of imaging slices 160 (planes). It should be noted that the PA array 110' is responsive both to emitted US reflections, and to PA reflections, which are similar except that they are induced by the laser 114 rather than the US transducer/sensor itself. As both the inner shaft 130 with the photoacoustic array 110', and the outer body 120 with the mirror 126 rotate independently, a full array of image slices 160 can be obtained for each position of the mirror 126 defining a perpendicular sensing axis 162 through step rotation of the array 110', discussed further below in FIG. 4.

Registration and alignment with a common frame occurs for the imaging slices 160 (imaging planes) of FIGS. 3A-3B. For the purpose of functional PA imaging, a technique called spectroscopic decomposition is utilized in this study. The received PA signals can be assumed as linear combinations of multiple absorbers in a tissue or contrast agents; therefore, the obtained signals can be decoupled into the contribution of each absorber by referring to their absorbing characteristics. This concept can be formularized as:

$$\text{argmin}_{m_{1,2,\ldots,M}} \left\| \sum_{w} \left( p - \sum_{i=1}^{M} m_i \mu_{a,i} \right) \right\|$$

where p is the obtained PA spectrum, $\mu_{a,i}$ and M are the absorption spectrum of the contrast i and M is the number of assumed optical absorbers. w is the applied laser wavelength. $m_i$ as the weight of the contract i, is calculated as an output of this equation.

Figure 4:
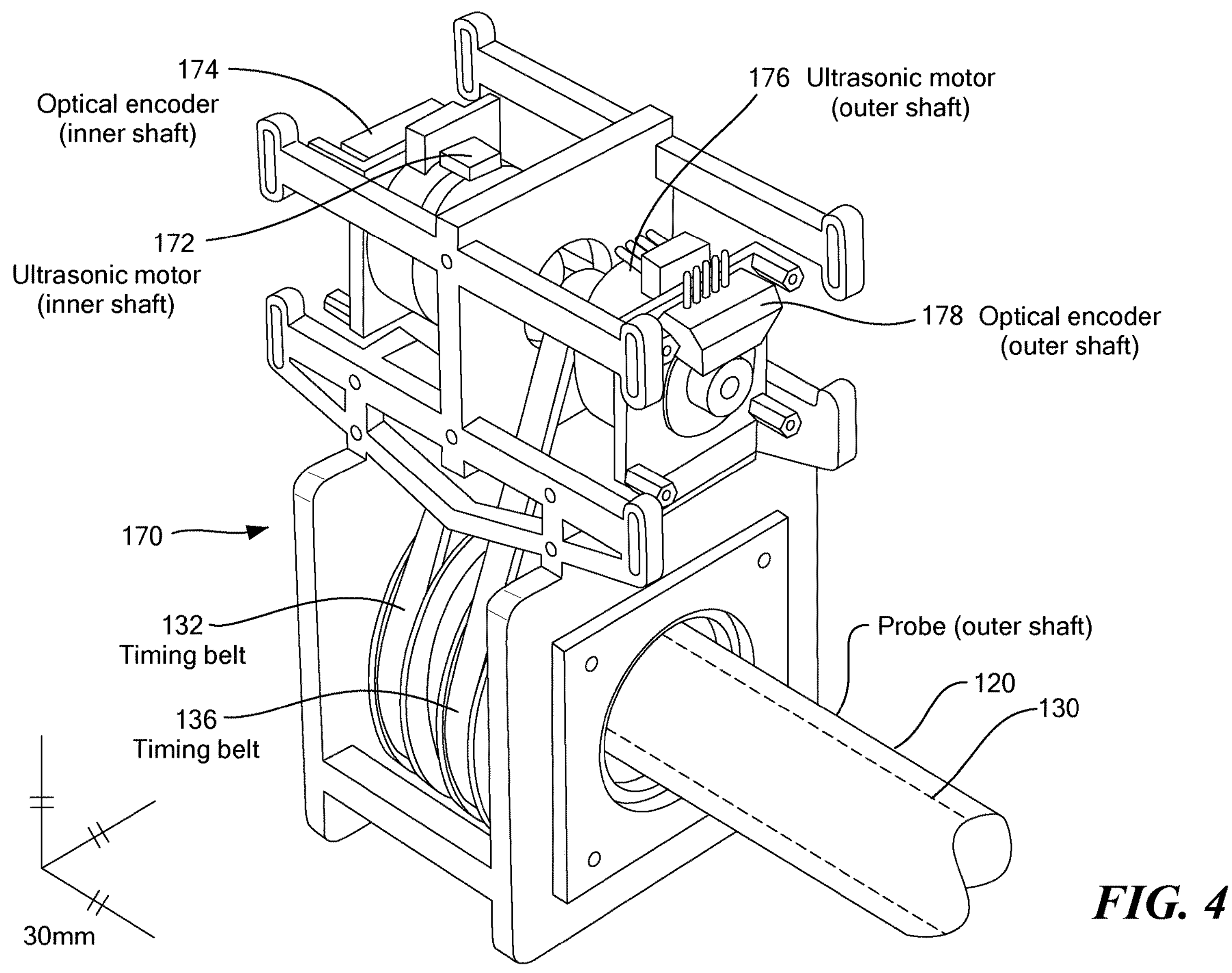
FIG. 4 shows a controller for directing the multi-mode imaging device of FIGS. 1 and 2.

FIG. 4 shows a controller for directing the multi-mode imaging device of FIGS. 1 and 2 in an MRI environment 103 using nonmagnetic materials. The probe 101 is driven by a probe drive circuit (FIG. 5 below) for rotating the elongated probe 101. The probe drive circuit is configured for rotating the reflective mirror 126 for alignment with an imaging plane defining each of image slices 160-N. The imaging plane is perpendicular to an axis of rotation 127 of the elongated probe 101. The photoacoustic array 110' defining the photoacoustic sensor 110 is configured for returning an imaging signal indicative of each imaging plane, during which the sensor drive circuit rotates the inner shaft 120 via an inner shaft motor 172 and guided by an inner shaft encoder 174. The photoacoustic array 110' is therefore configured for gathering an image signal indicative of an imaging plane (slice 160) based on orientation of the photoacoustic array due to rotation of the inner shaft 130. For each series of imaging slices 160-1 . . . 160-N, step rotation of the probe 120 orients the sensing axis 162 at another orientation via the outer shaft motor 176 driven based on outer shaft encoder 178. Engagement with the shafts 120, 130 is provided by inner shaft belt 132 and outer shaft belt 136.

The MRI-compatible probe actuation module is developed and fabricated with MRI-safe material and MRI-conditional electronics. The motors 172, 176 may be ultrasonic motor used as an actuator, ensuring compatibility with MRI by precluding the use of magnetic materials. The timing belt 132, 136 system is used to transfer the movement from the motor to the inner shaft 130 and outer shaft 120, typically with a predetermined ratio of 5:1. Optical encoders 174, 178 mount on the back shaft of each motor to monitor the rotation of the shaft, which is converted corresponding to the predetermined ratio.

Figure 5:
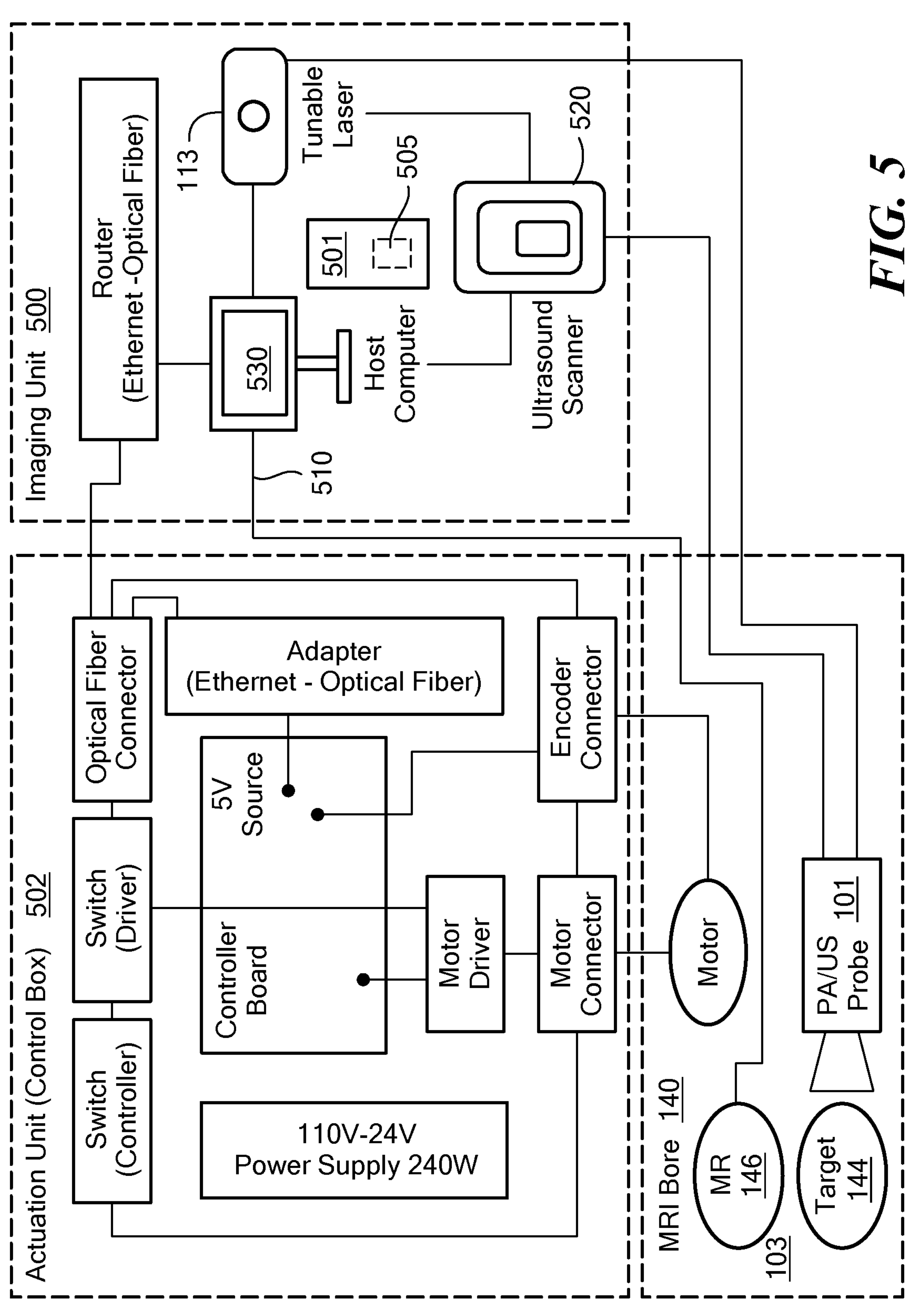
FIG. 5 is a block diagram of a system and control circuit for operating the multi-mode imaging device of FIGS. 1-4.

FIG. 5 is a block diagram of a system and control circuit for operating the multi-mode imaging device of FIGS. 1-4. Referring to FIGS. 1-5, the imaging system 150 includes an imaging circuit 500 and a control circuit 502. The imaging circuit 500 includes a computing device 501 further including an interface 510 for receiving a first imaging signal from the first imaging modality, and an interface 520 for receiving a second imaging signal from the second imaging modality. An application 505 on the computing device 501 registers the first imaging signal and the second imaging signal with a common frame of reference for rendering the combined image 530.

In the system for magnetic tolerant, multi-mode imaging, the elongated probe 101 is disposed into an imaging region 103 for a target 144 region of interest of a first imaging modality defined by an MRI 146 sensory apparatus. In the example configuration, this is a PCa patient 148 using a transrectal probe. The application 505 receives a returned imaging signal in the first imaging modality from the region of interest 103. The imaging sensor 110 in rotational communication with the elongated probe 101 is rotated, where the imaging sensor 110 is responsive to a second imaging modality such as PA and/or US. The transrectal probe 101 directs an imaging signal in the second imaging modality from the rotating imaging sensor at the region of interest. The application 505 captures a returned imaging signal in the second imaging modality from the region of interest. The application 505 aligns the respective imaging signals from the first and second imaging modality for registering a combined image in a common frame of reference, and renders the combined image 530.

Those skilled in the art should readily appreciate that the programs and methods defined herein are deliverable to a user processing and rendering device in many forms, including but not limited to a) information permanently stored on non-writeable storage media such as ROM devices, b) information alterably stored on writeable non-transitory storage media such as solid state drives (SSDs) and media, flash drives, floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions, including virtual machines and hypervisor controlled execution environments. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A magnetic tolerant, multi-mode imaging device, comprising:

an elongated probe adapted for insertion into an imaging region of a first imaging modality the elongated probe further including:

a body having a tapered or rounded distal end adapted for insertion into an imaging subject defining the region of interest; and an inner shaft disposed within a bore of the body;

an imaging sensor in rotational communication with the elongated probe, the imaging sensor disposed on the inner shaft for rotation and responsive to a second imaging modality;

a reflective mirror disposed on the body distal from the inner shaft, the reflective mirror configured for reflecting an image signal of the second imaging modality; a photoacoustic laser disposed on the inner shaft for emanating a laser signal, the reflective mirror disposed for directing the laser signal based on an angle of the reflective mirror;

a control circuit configured for activating the first imaging modality and the second imaging modality for imaging over a region of interest; and an imaging circuit for aligning images received from the first and second imaging modalities for rendering a combined image, the second imaging modality defined by an array of image planes obtained from respective step rotation positions of the imaging sensor reflected via the reflective mirror defining a perpendicular sensing axis.

2. The method of claim 1 wherein the imaging circuit further comprises:

an interface for receiving a first imaging signal from the first imaging modality;

an interface for receiving a second imaging signal from the second imaging modality;

the imaging circuit for registering the first imaging signal and the second imaging signal with a common frame of reference for rendering the combined image.

3. The method of claim 2 wherein the first imaging modality is magnetic resonance imaging and the elongated probe is disposed in an imaging region of a magnetic resonance region.

4. The method of claim 1 wherein the body further comprises:

a void in the body for allowing reflection of the laser signal into the region of interest;

the inner shaft having a photoacoustic sensor defining the imaging sensor, the photoacoustic sensor aligned with the reflective mirror and the photoacoustic laser for receiving reflected photoacoustic signals from the region of interest.

5. The method of claim 4 further comprising:

a photoacoustic array defining the photoacoustic sensor, the photoacoustic array configured for returning an imaging signal indicative of an imaging plane; and a sensor drive circuit for rotating the inner shaft about an axis for gathering a set of imaging planes.

6. The method of claim 4 further comprising:

a probe drive circuit for rotating the elongated probe, the probe drive circuit configured for rotating the reflective mirror for alignment with an imaging plane, the imaging plane perpendicular to an axis of rotation of the elongated probe;

a photoacoustic array defining the photoacoustic sensor, the photoacoustic array configured for returning an imaging signal indicative of an imaging plane; and a sensor drive circuit for rotating the inner shaft, the photoacoustic array configured for gathering an image signal indicative of an imaging plane based on orientation of the photoacoustic array due to rotation of the inner shaft.

7. The method of claim 1 wherein the body and the inner shaft are formed from magnetic tolerant materials.

8. The method of claim 1 wherein the elongated probe is formed from non-magnetic materials.

9. A multi-mode imaging system, comprising:

an elongated probe adapted for insertion into a magnetic resonance imaging region, the elongated probe including:

a body having a tapered or rounded distal end adapted for insertion into an imaging subject defining the region of interest; and an inner shaft disposed within a bore of the body;

a photoacoustic imaging array attached to the inner shaft and in rotational communication with the elongated probe, the photoacoustic imaging array responsive to photoacoustic signals for generating an imaging plane;

a reflective mirror attached at a distal end of the body adjacent the photoacoustic imaging array, the inner shaft configured for rotation independently of the reflective mirror for varying the imaging plane about an axis and the reflective mirror configured for reflecting a photoacoustic imaging signal to the photoacoustic imaging array;

a photoacoustic laser disposed on the inner shaft for emanating a laser signal directed at the reflective mirror, the reflective mirror disposed for directing the laser signal based on an angle of the reflective mirror; and an imaging circuit for aligning images received from the imaging plane with an imaging signal based on the magnetic resonance imaging for rendering a combined image, the photoacoustic imaging signal defined by an array of image planes obtained from respective step rotation positions of the photoacoustic imaging array reflected via the reflective mirror defining a perpendicular sensing axis.

10. A method for magnetic tolerant, multi-mode imaging, comprising:

disposing an elongated probe into an imaging region for a region of interest of a first imaging modality, the elongated probe further including:

a body having a tapered or rounded distal end adapted for insertion into an imaging subject defining the region of interest; and an inner shaft rotatably disposed within a bore of the body;

receiving a returned imaging signal in the first imaging modality from the region of interest;

rotating an imaging sensor in rotational communication with the elongated probe, the imaging sensor responsive to a second imaging modality and disposed on the inner shaft for rotation;

directing an imaging signal in the second imaging modality from the rotating imaging sensor at the region of interest;

capturing a returned imaging signal in the second imaging modality from the region of interest by reflecting, via a reflective mirror disposed on the body distal from the inner shaft, the reflective mirror configured for reflecting the returned image signal of the second imaging modality, the returned imaging signal defined by an array of image planes obtained from respective step rotation positions of the photoacoustic imaging array reflected via the reflective mirror defining a perpendicular sensing axis;

aligning the respective imaging signals from the first and second imaging modalities for registering a combined image in a common frame of reference, the second imaging modality defined by an array of image planes obtained from respective step rotation positions of the imaging sensor reflected via the reflective mirror defining a perpendicular sensing axis; and rendering the combined image.

11. The method of claim 10 wherein the first imaging modality further comprises a magnetic resonance imaging (MRI) medium directed at a region of interest in an MRI bore; and the second imaging modality further comprises a photoacoustic medium including a laser signal and returned ultrasound defining the returned imaging signal in the second imaging modality.

12. The method of claim 10 wherein aligning images further comprises:

receiving a first imaging signal from the first imaging modality;

receiving a second imaging signal from the second imaging modality;

registering the first imaging signal and the second imaging signal with a common frame of reference for rendering the combined image.

13. A computer program embodying program code on a non-transitory computer readable storage medium that, when executed by a processor, performs steps for implementing a method for magnetic tolerant, multi-mode imaging, the method comprising:

disposing an elongated probe into an imaging region for a region of interest of a first imaging modality, the elongated probe further including:

a body having a tapered or rounded distal end adapted for insertion into an imaging subject defining the region of interest; and an inner shaft rotatably disposed within a bore of the body;

receiving a returned imaging signal in the first imaging modality from the region of interest;

rotating an imaging sensor in rotational communication with the elongated probe, the imaging sensor responsive to a second imaging modality and disposed on the inner shaft for rotation;

directing an imaging signal in the second imaging modality from the rotating imaging sensor at a region of interest;

capturing a returned imaging signal in the second imaging modality from the region of interest by reflecting, via a reflective mirror disposed on the body distal from the inner shaft, the reflective mirror configured for reflecting the returned image signal of the second imaging modality the returned imaging signal defined by an array of image planes obtained from respective step rotation positions of the photoacoustic imaging array reflected via the reflective mirror defining a perpendicular sensing axis;

aligning the respective imaging signals from the first and second imaging modality for registering a combined image in a common frame of reference, the second imaging modality defined by a photoacoustic laser disposed on the inner shaft for emanating a laser signal, the reflective mirror disposed for directing the laser signal based on an angle of the reflective mirror; and rendering the combined image.

* * * * *